United States Patent
Boice et al.

(10) Patent No.: US 8,404,695 B2
(45) Date of Patent: Mar. 26, 2013

(54) PYRIMIDINYL PYRIDONE INHIBITORS OF JNK

(75) Inventors: Genevieve N. Boice, Palo Alto, CA (US); Leyi Gong, San Mateo, CA (US); Kristen Lynn McCaleb, Daly City, CA (US); Wylie Solang Palmer, Mountain View, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 612 days.

(21) Appl. No.: 12/603,726

(22) Filed: Oct. 22, 2009

(65) Prior Publication Data
US 2010/0099691 A1    Apr. 22, 2010

Related U.S. Application Data

(60) Provisional application No. 61/107,532, filed on Oct. 22, 2008.

(51) Int. Cl.
| | | |
|---|---|---|
| C07D 471/04 | (2006.01) | |
| A61K 31/519 | (2006.01) | |
| A61P 35/00 | (2006.01) | |
| A61P 19/00 | (2006.01) | |
| A61P 29/00 | (2006.01) | |
| A61P 37/08 | (2006.01) | |
| A61P 3/10 | (2006.01) | |
| A61P 25/28 | (2006.01) | |
| A61P 25/16 | (2006.01) | |
| A61P 35/02 | (2006.01) | |

(52) U.S. Cl. ............... 514/264.11; 544/279
(58) Field of Classification Search ........ 544/279; 514/264.11
See application file for complete search history.

(56) References Cited

U.S. PATENT DOCUMENTS
2004/0224958 A1    11/2004    Booth et al.
2012/0059002 A1*    3/2012    Hansen et al. ............ 514/234.5

FOREIGN PATENT DOCUMENTS
WO    9833798 A2    8/1998
WO    0155148       8/2001

OTHER PUBLICATIONS

International Search Rerport for PCT/EP2009/063327 dated Jul. 29, 2010.
Barvian, M., et. al. "Pyrido[2,3-d]pyrimidin-7-one Inhibitors of Cyclin-Dependent Kinases," Journal of Medicinal Chemistry, 2000, vol. 43, pp. 4606-4616.
Caballero, J., et. al. "Structural requirements of pyrido[2,3-d]pyrimidin-7-one as CDK4/D inhibitors: 2D autocorrelation, CoMFA and CoMSIA analyses," Bioorganic & Medicinal Chemistry, 2008, vol. 16, pp. 6103-6115.

* cited by examiner

*Primary Examiner* — Susanna Moore
*Assistant Examiner* — Cecilia M Jaisle
(74) *Attorney, Agent, or Firm* — George W. Johnston; Dennis P. Tramaloni; Jennifer L. Kisko

(57) ABSTRACT

This application discloses novel pyrimidinyl pyridone derivatives according to Formula I,

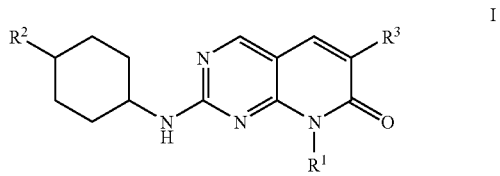

wherein $R^1$, $R^2$, and $R^3$ are defined as described herein, which inhibit JNK. The compounds disclosed herein are useful to modulate the activity of JNK and treat diseases associated with excessive JNK activity. The compounds are useful to treat autoimmune, inflammatory, metabolic, and neurological diseases as well as cancer. Also disclosed are compositions comprising the compound of Formula I and methods of treatment comprising administering a therapeutically effective amount of the compound of Formula I to a subject in need thereof.

7 Claims, No Drawings

PYRIMIDINYL PYRIDONE INHIBITORS OF JNK

CROSS-REFERENCE TO RELATED APPLICATIONS

This application is entitled to the benefit of U.S. provisional patent application Ser. No. 61/107,532 filed on Oct. 22, 2008, the disclosure of which is incorporated herein by reference.

FIELD OF THE INVENTION

This invention relates generally to the fields of medicinal chemistry and treatment of inflammatory disorders. More particularly, the invention relates to pyrimidinyl pyridone inhibitors of JNK, methods and formulations for inhibiting JNK and treating JNK-mediated disorders, and the like.

BACKGROUND OF THE INVENTION

JNK The c-Jun N-terminal kinases (JNKs) are members of mitogen-activated protein kinase family along with p38 and extracellular signal-regulated kinases (ERKs). Three distinct genes (jnk1, jnk2 and jnk3) encoding 10 splice variants have been identified. JNK1 and JNK2 are expressed in a wide variety of tissues, whereas JNK3 is mainly expressed in neurons, and to a lesser extent in heart and testes. Members of JNK family are activated by pro-inflammatory cytokines such as tumor necrosis factor $\alpha$ (TNF-$\alpha$) and interleukin-1$\beta$ (IL-1$\beta$), as well as environmental stresses. The activation of JNKs is mediated by its upstream kinases, MKK4 and MKK7, via dual phosphorylation of Thr-183 and Tyr-185. It has been shown that MKK4 and MKK7 can be activated by the diverse upstream kinases, including MEKK1 and MEKK4, depending upon the external stimuli and cellular context. The specificity of JNK signaling is achieved by forming a JNK-specific signaling complex containing multiple components of the kinase cascade by use of scaffold proteins called JNK-interacting proteins. JNKs have been shown to play important roles in inflammation, T cell functions, apoptosis and cellular survival by phosphorylating specific substrates, including transcription factors such as c-Jun, the component of activator protein-1 (AP1) family, and ATF2, as well as non-transcription factors such as IRS-1 and Bcl-2. Over-activation of JNK is believed to be an important mechanism in autoimmune, inflammatory, metabolic, neurological diseases as well as cancer.

Rheumatoid arthritis (RA) is a systemic autoimmune disease characterized by chronic inflammation of the joints. In addition to the joint swelling and pain caused by the inflammatory process, most RA patients ultimately develop debilitating joint damage and deformation. Several lines of compelling pharmacological and genetic evidence in cellular and animal models strongly suggest the relevance and importance of the activated JNK in the pathogenesis of RA. First, abnormal activation of JNK was detected in both human arthritic joints from RA patients and rodent arthritic joints from animal models of arthritis. In addition, inhibition of JNK activation by selective JNK inhibitors blocked proinflammatory cytokines and MMP production in human synoviocytes, macrophages and lymphocytes. Importantly, administration of the selective JNK inhibitors in rats with adjuvant arthritis or in mice with collagen-induced arthritis effectively protected joints from destruction and significantly reduced paw swelling by inhibiting cytokine and collagenase expression.

Asthma is a chronic inflammatory disease of airways, characterized by the presence of a cellular inflammatory process and by bronchial hyper-responsiveness associated with structural changes of the airways. This disorder has been shown to be driven by many cell types in the airways, including T lymphocytes, eosinophils, mast cells, neutrophils and epithelial cells. JNKs have emerged as promising therapeutic targets for asthma based upon the recent proof-of-concept studies: it has been shown that JNK inhibitors significantly blocked RANTES production in activated human airway smooth cells. More importantly, the JNK inhibitors showed good efficacy in chronic rat and mouse models for their abilities to reduce cellular infiltration, inflammation, hyper-responsiveness, smooth muscle proliferation, and IgE production. These observations suggest important roles of JNKs in the allergic inflammation, airway remodeling process associated with hyper-responsiveness. Therefore, blockade of JNK activity is expected to be beneficial for the treatment of asthma.

Type 2 diabetes is the most serious and prevalent metabolic disease characterized by insulin resistance and insulin secretion impairment as a result of chronic low-level inflammation and abnormal lipid metabolism associated with oxidative stress. It has been reported that JNK activity is abnormally elevated in various diabetic target tissues under obese and diabetic conditions. Activation of the JNK pathway by pro-inflammatory cytokines and oxidative stresses negatively regulates insulin signaling via phosphorylation of insulin receptor substrate-1 (IRS-1) at $Ser^{307}$, therefore contributes to insulin resistance and glucose tolerance. Compelling genetic evidence came from elegant animal model studies using $jnk^{-/-}$ mice crossed with either genetic (ob/ob) obese mice or dietary obese mice. Loss of JNK1 ($JNK1^{-/-}$), but not JNK2 functions ($jnk2^{-/-}$), protected obese mice from body gains, increased steady-state levels of blood glucose, and decreased plasma insulin levels. These studies demonstrated the potential utility of JNK inhibitor in the treatment of obesity/type 2 diabetes.

Neurodegenerative diseases, such as Alzheimer's (AD), Parkinson's (PD) and Stroke are CNS diseases characterized by synaptic loss, neuronal atrophy and death. The JNK pathway leading to c-Jun activation has been shown to play a causal role in apoptosis of isolated primary embryonic neurons and multiple neuronal cell lines upon induction of a variety of stimuli. Over-activation of JNK was observed in human brains from AD patients or rodent brain sections derived from animal models of neurodegenerative diseases. For example, increased phospho-JNKs were detected in the post-mortem brains from the AD patients. Administration of JNK inhibitory peptide (JIP-1 peptide) in the rodent model of AD induced by $\beta$-amyloid peptide administration prevented the impairment of synaptic plasticity. In the animal models of PD (MPTP model), elevated phospho-MKK4 and phospho-JNKs were observed concomitantly with the neuronal cell death. Adenoviral gene transfer of JNK inhibitory peptide (JIP-1 peptide) into striatum of mice attenuated behavioral impairment by inhibiting MPTP-mediated JNK, c-Jun and caspase activation, therefore blocking neuronal cell death in the substantia nigra. In addition, in the animal model of ischemic stroke induced by glutamate excitotoxicity, mice deficient in JNK3, but not JNK1 or JNK2, were resistant to kainic acid (glutamate receptor agonist)-mediated seizure or neuronal death. These data suggest JNK3 was mainly responsible for glutamate excitotoxicity, an important component in ischemic conditions. Taken together, data has emerged suggesting JNKs as attractive target for multiple CNS diseases associated with neuronal cell death.

Uncontrolled cellular growth, proliferation and migration along with de-regulated angiogenesis lead to the formation of malignant tumors. The JNK signal transduction pathway may not act exclusively in apoptosis, sustained JNK activation leading to AP1 activation has recently been implicated to contribute to the cellular survival of specific cancer types such as glial tumors and BCL-ABL transformed B lymphoblasts. In the case of glial tumors, enhanced JNK/AP1 activity was seen in most of the primary brain tumor samples. For the transformed B lymphoblasts, BCL-ABL was shown to activate the JNK pathway which in turn up-regulated expression of anti-apoptotic bcl-2 gene. Interestingly, the multi-drug resistance and hyper-proliferation seen in treatment-refractory AML (acute myeloid leukemia) patients has been causally linked to the sustained JNK activity present in these AML samples. Activation of JNK in leukemic cells resulted in induced expression of efflux pumps such as mdr1 and MRP1 responsible for multidrug resistance. Also, genes with a survival benefit in response to oxidative stress including glutathione-S-transferase π and γ-glutamyl cysteine synthase were also upregulated by the activated JNK pathway.

Accordingly, JNK modulators are useful in treating a variety of diseases and/or conditions. The role of cyclin-dependent kinases ("cdks") in the regulation of cellular proliferation is well established. There is an extensive body of literature validating the use of compounds that inhibit targets in the Cdk4, Cdk2 and Cdk1 pathways as anti-proliferative therapeutic agents. See, e.g., J. Lukas et al., *Nature* (1995) 79:573-82; J. R. Nevins, *Science* (1992) 258:424-29; I. K. Lim et al., *Mol Carcinogen* (1998) 23:25-35; S. W. Tam et al., *Oncogene* (1994) 9:2663-74; B. Driscoll et al., *Am. J. Physiol.* (1997) 273 (*Lung Cell. Mol. Physiol.*) L941-L949; and J. Sang et al., *Chin. Sci. Bull.* (1999) 44:541-44. Inhibitors of cellular proliferation act as reversible cytostatic agents that are useful in the treatment of disease processes which feature abnormal cellular growth, such as cancers and other cell proliferative disorders including, for example inflammation (e.g. benign prostate hyperplasia, familial adenomauosis, polyposis, neuro-fibromatosis, atherosclerosis, pulmonary fibrosis, arthritis, psoriasis, inflammatory bowel disease, transplantation rejections infections), viral infections (including, without limitation, herpesvirus, poxvirus, Epstein-Barr virus), autoimmune disease (e.g. lupus, rheumatoid arthritis, psoriasis, inflammatory bowel disease), neurodegenerative disorders (including, without limitation, Alzheimer's disease), and neurodegenerative diseases (e.g. Parkinson's disease, amyotrophic lateral sclerosis, retinitis pigmentosa, spinal muscular atrophy, and cerebral degeneration).

SUMMARY OF THE INVENTION

The application provides a compound of formula I

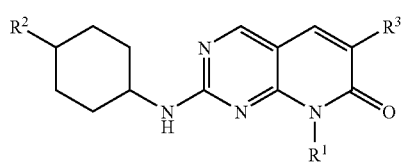

wherein:

$R^1$ is —Y—$R^{1'}$;

Y is lower alkylenyl, cycloalkyl, heterocycloalkyl, or phenyl;

$R^{1'}$ is H, hydroxy, OC(=O)$R^{1'''}$, NHC(=O)$R^{1'''}$, C(=O)O$R^{1'''}$, NHSO$_2$$R^{1'''}$, or N($R^{1''''}$)$_2$, $R^{1'''}$ is H, lower alkyl, amino, or lower haloalkyl;

each $R^{1''''}$ is independently H or lower alkyl;

$R^2$ is H or $R^{2'}$;

$R^{2'}$ is hydroxy, N($R^{2''}$)$_2$, NHSO$_2$$R^{2''}$ or amido;

each $R^{2''}$ is independently H or lower alkyl; and $R^3$ is H or methyl;

with the proviso that when Y is ethyl or cyclohexyl, $R^2$ is H, and $R^3$ is H, then $R^{1'}$ is not H.

In certain embodiments of Formula I, Y is lower alkylenyl.

In certain embodiments of Formula I, $R^2$ is H.

In certain embodiments of Formula I, Y is cycloalkyl and $R^{1'}$ is H.

In certain embodiments of Formula I, Y is heterocycloalkyl and $R^{1'}$ is H.

The application provides the compound of Formula I, selected from the group consisting of:

2-Cyclohexylamino-8-(3-hydroxy-1-methyl-propyl)-8H-pyrido[2,3-d]pyrimidin-7-one;
2-Cyclohexylamino-8-(3-hydroxy-propyl)-8H-pyrido[2,3-d]pyrimidin-7-one;
2-Cyclohexylamino-8-cyclopentyl-8H-pyrido[2,3-d]pyrimidin-7-one;
2-(4-Hydroxy-cyclohexylamino)-8-(3-hydroxy-propyl)-8H-pyrido[2,3-d]pyrimidin-7-one;
N-{4-[8-(3-Hydroxy-propyl)-7-oxo-7,8-dihydro-pyrido[2,3-d]pyrimidin-2-ylamino]-cyclohexyl}-methanesulfonamide;
8-Butyl-2-cyclohexylamino-8H-pyrido[2,3-d]pyrimidin-7-one;
2-(4-Hydroxy-cyclohexylamino)-8-(3-hydroxy-propyl)-6-methyl-8H-pyrido[2,3-d]pyrimidin-7-one;
4-(2-Cyclohexylamino-7-oxo-7H-pyrido[2,3-d]pyrimidin-8-yl)-piperidine-1-carboxylic acid tert-butyl ester;
N-[3-(2-Cyclohexylamino-7-oxo-7H-pyrido[2,3-d]pyrimidin-8-yl)-propyl]-methanesulfonamide;
N-{4-[8-(3-Hydroxy-propyl)-7-oxo-7,8-dihydro-pyrido[2,3-d]pyrimidin-2-ylamino]-cyclohexyl}-acetamide;
2-Cyclohexylamino-8-(3-hydroxy-propyl)-6-methyl-8H-pyrido[2,3-d]pyrimidin-7-one;
Acetic acid 3-(2-cyclohexylamino-7-oxo-7H-pyrido[2,3-d]pyrimidin-8-yl)-propyl ester;
2-Cyclohexylamino-8-methyl-8H-pyrido[2,3-d]pyrimidin-7-one;
N-[3-(2-Cyclohexylamino-7-oxo-7H-pyrido[2,3-d]pyrimidin-8-yl)-propyl]-2,2,2-trifluoro-acetamide;
N-[3-(2-Cyclohexylamino-7-oxo-7H-pyrido[2,3-d]pyrimidin-8-yl)-propyl]-N,N-dimethylaminosulfonamide;
8-(4-Chloro-phenyl)-2-cyclohexylamino-8H-pyrido[2,3-d]pyrimidin-7-one
2-(4-Hydroxy-cyclohexylamino)-8-((S)-2-hydroxy-propyl)-8H-pyrido[2,3-d]pyrimidin-7-one;
2-(4-Amino-cyclohexylamino)-8-(3-hydroxy-propyl)-8H-pyrido[2,3-d]pyrimidin-7-one;
2-(4-Hydroxy-cyclohexylamino)-8-methyl-8H-pyrido[2,3-d]pyrimidin-7-one;
2-(4-Hydroxy-cyclohexylamino)-8-((S)-2-hydroxy-propyl)-8H-pyrido[2,3-d]pyrimidin-7-one;
8-(3-Amino-propyl)-2-cyclohexylamino-8H-pyrido[2,3-d]pyrimidin-7-one;
2-(4-Hydroxy-cyclohexylamino)-6,8-dimethyl-8H-pyrido[2,3-d]pyrimidin-7-one;
2-Cyclohexylamino-8-piperidin-4-yl-8H-pyrido[2,3-d]pyrimidin-7-one;
2-Cyclohexylamino-8-(1-methyl-piperidin-4-yl)-8H-pyrido[2,3-d]pyrimidin-7-one; and
2-Cyclohexylamino-8-(3-dimethylamino-propyl)-8H-pyrido[2,3-d]pyrimidin-7-one.

The application provides a compound of Formula II

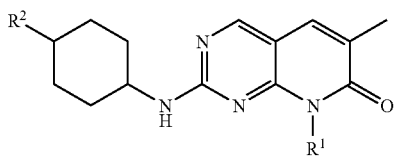

wherein:
R¹ is —Y—R¹';
Y is lower alkylenyl, cycloalkyl, heterocycloalkyl, or phenyl;
R¹' is H, hydroxy, amino, NHSO₂R¹''', OC(=O)R¹''', NHC(=O)R¹''', or C(=O)OR¹''';
R¹''' is H, lower alkyl, amino, or lower haloalkyl;
R² is H or R²';
R²' is hydroxy or amino; and
with the proviso that when R² is H and R¹' is heterocycloalkyl, then R¹''' is not H.

In certain embodiments of Formula II, Y is lower alkylenyl.
In certain embodiments of Formula II, R² is hydroxy.
In certain embodiments of Formula II, R¹' is hydroxy.

In one aspect, the application provides a method of treating a JNK-mediated disorder in a subject having a JNK-mediated disorder, said method comprising administering to a subject in need thereof a therapeutically effective amount of any of the above compounds of Formulae I-II.

In certain embodiments of the method of treating a JNK-mediated disorder, the JNK-mediated disorder is characterized by cellular proliferation.

In certain embodiments of the method of treating a JNK-mediated disorder, the JNK-mediated disorder is arthritis.

In certain embodiments of the method of treating a JNK-mediated disorder, the arthritis is rheumatoid arthritis.

In certain embodiments of the method of treating a JNK-mediated disorder, the JNK-mediated disorder is asthma.

In certain embodiments of the method of treating a JNK-mediated disorder, the JNK-mediated disorder is diabetes.

In certain embodiments of the method of treating a JNK-mediated disorder, the JNK-mediated disorder is Alzheimer's disease.

In certain embodiments of the method of treating a JNK-mediated disorder, the JNK-mediated disorder is Parkinson's disease.

In certain embodiments of the method of treating a JNK-mediated disorder, the JNK-mediated disorder is ischemic stroke.

In certain embodiments of the method of treating a JNK-mediated disorder, the JNK-mediated disorder is cancer.

In certain embodiments of the method for treating a JNK-mediated disorder, wherein the JNK-mediated disorder is cancer, the cancer is brain cancer.

In certain embodiments of the method for treating a JNK-mediated disorder, wherein the JNK-mediated disorder is cancer, the cancer is leukemia.

DETAILED DESCRIPTION OF THE INVENTION

All publications cited in this disclosure are incorporated herein by reference in their entirety.
Definitions
Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise. Thus, the phrase "'a' or 'an' entity' as used herein refers to one or more of that entity; for example, a compound refers to one or more compounds or at least one compound. As such, the terms "a" (or "an"), "one or more", and "at least one" can be used interchangeably herein.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., R¹, R²) occurs more than one time in any moiety or formula depicting and describing compounds employed or claimed in the present invention, its definition on each occurrence is independent of its definition at every other occurrence. Also, combinations of substituents and/or variables are permissible only if such combinations result in stable compounds.

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Certain compounds of the invention may exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇌ —C(—

OH)=CH—), amide/imidic acid (—C(=O)—NH— ⇌ —C(—OH)=N—) and amidine (—C(=NR)—NH— ⇌ —C(—NHR)=N—) tautomers. The latter two are particularly common in heteroaryl and heterocyclic rings and the present invention encompasses all tautomeric forms of the compounds.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10$^{th}$ Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group.

The term "acyl" as used herein denotes a group of formula —C(=O)R wherein R is hydrogen or lower alkyl as defined herein. The term or "alkylcarbonyl" as used herein denotes a group of formula C(=O)R wherein R is alkyl as defined herein.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons.

The term "alkylene" or "alkylenyl" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., -CHMe- or —CH$_2$CH(i-Pr)CH$_2$—), unless otherwise indicated. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an —O-alkyl wherein alkyl is $C_{1-10}$.

The term "amino" as used herein refers to a group of formula —NR$_2$ wherein each R is independently H or lower alkyl as defined herein.

The term "amido" as used herein refers to a group of formula —NHC(=O)R wherein R is lower alkyl as defined herein.

"Cycloalkyl" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated.

The term "heterocyclyl", "heterocycle", or "heterocycloalkyl" as used herein denotes a monovalent saturated cyclic radical, consisting of one or more rings, preferably one to two rings, of three to eight atoms per ring, incorporating one or more ring heteroatoms (chosen from N, O or $S(O)_{0-2}$).

The term "hydroxyalkyl" as used herein denotes an alkyl radical as herein defined wherein one to three hydrogen atoms on different carbon atoms is/are replaced by hydroxyl groups.

Commonly used abbreviations include: acetyl (Ac), azo-bis-isobutyrylnitrile (AIBN), atmospheres (Atm), 9-borabicyclo[3.3.1]nonane (9-BBN or BBN), tert-butoxycarbonyl (Boc), di-tent-butyl pyrocarbonate or boc anhydride (BOC$_2$O), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N, N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), ethyl (Et), ethyl acetate (EtOAc), ethanol (EtOH), 2-ethoxy-2H-quinoline-1-carboxylic acid ethyl ester (EEDQ), diethyl ether (Et$_2$O), O-(7-azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), lithium hexamethyl disilazane (LiHMDS), methanol (MeOH), melting point (mp), MeSO$_2$— (mesyl or Ms), methyl (Me), acetonitrile (MeCN), m-chloroperbenzoic acid (MCPBA), mass spectrum (ms), methyl t-butyl ether (MTBE), N-bromosuccinimide (NBS), N-carboxyanhydride (NCA), N-chlorosuccinimide (NCS), N-methylmorpholine (NMM), N-methylpyrrolidone (NMP), pyridinium chlorochromate (PCC), pyridinium dichromate (PDC), phenyl (Ph), propyl (Pr), iso-propyl (i-Pr), pounds per square inch (psi), pyridine (pyr), room temperature (rt or RT), tert-butyldimethylsilyl or t-BuMe$_2$Si (TBDMS), triethylamine (TEA or Et$_3$N), 2,2,6,6-tetramethylpiperidine 1-oxyl (TEMPO), triflate or CF$_3$SO$_2$— (TO, trifluoroacetic acid (TFA), 1,1'-bis-2,2,6,6-tetramethylheptane-2,6-dione (TMHD), O-benzotriazol-1-yl-N,N,N', N'-tetramethyluronium tetrafluoroborate (TBTU), thin layer chromatography (TLC), tetrahydrofuran (THF), trimethylsilyl or Me$_3$Si (TMS), p-toluenesulfonic acid monohydrate (TsOH or pTsOH), 4-Me-C$_6$H$_4$SO$_2$— or tosyl (Ts), N-urethane-N-carboxyanhydride (UNCA). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford).

The terms "halo," "halogen," and "halide" are used interchangeably herein and refer to fluoro, chloro, bromo, and iodo.

"Haloalkyl" means alkyl as defined herein in which one or more hydrogen has been replaced with same or different halogen.

"Heterocyclyl" or "heterocycloalkyl" means a monovalent saturated moiety, consisting of one to two rings, incorporating one, two, or three or four heteroatoms (chosen from nitrogen, oxygen or sulfur). The heterocyclyl ring may be optionally substituted as defined herein.

"Optionally substituted" means a substituent which is substituted independently with zero to three substituents selected from lower alkyl, halo, OH, cyano, amino, nitro, lower alkoxy, or halo-lower alkyl.

"Leaving group" means a group with the meaning conventionally associated with it in synthetic organic chemistry, i.e., an atom or group displaceable under substitution reaction conditions.

"Optional" or "optionally" means that the subsequently described event or circumstance may but need not occur, and that the description includes instances where the event or circumstance occurs and instances in which it does not.

"Agonist" refers to a compound that enhances the activity of another compound or receptor site.

"Antagonist" refers to a compound that diminishes or prevents the action of another compound or receptor site.

The term "drug candidate" refers to a compound or preparation which is to be tested for possible effect in the treatment of a disease state in an animal, regardless of whether said drug candidate has any known biological activity.

The term "homologous" as used herein refers to a protein that performs substantially the same function in another subject species and shares substantial sequence identity, to the extent that they are recognized in the art as being different versions of the same protein, differing primarily in the species in which they are found. Thus, for example, human ERG, mouse ERG, and rat ERG are all considered homologous to each other.

"Modulator" means a molecule that interacts with a target. The interactions include, but are not limited to, agonist, antagonist, and the like, as defined herein.

"Disease" and "Disease state" means any disease, condition, symptom, disorder or indication.

The term "cell line" refers to a clone of immortalized mammalian cells. A "stable" cell line is a cell line that exhibits substantially consistent characteristics over time (e.g., with each doubling). A stable cell line within the scope of this invention provides a substantial proportion of cells that are capable of providing a seal resistance of greater than about 50 MOhm, a current amplitude of greater than about 200 pA, and provide a current amplitude that does not vary by more than approximately 20% over one hour under control conditions.

"Pharmaceutically acceptable salts" of a compound means salts that are pharmaceutically acceptable, as defined herein, and that possess the desired pharmacological activity of the parent compound. Such salts include:

(1) acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or (2) salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

It should be understood that all references to pharmaceutically acceptable salts include solvent addition forms (solvates) or crystal forms (polymorphs) as defined herein, of the same acid addition salt.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" includes mammals and birds. "Mammals" means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgement of the attending medical or veterinary practitioner, and other factors.

"Pharmacological effect" as used herein encompasses effects produced in the subject that achieve the intended purpose of a therapy. For example, a pharmacological effect would be one that results in the prevention, alleviation or reduction of urinary incontinence in a treated subject.

"Disease state" means any disease, condition, symptom, or indication.

"Treating" or "treatment" of a disease state includes (i) preventing the disease state, i.e. causing the clinical symptoms of the disease state not to develop in a subject that may be exposed to or predisposed to the disease state, but does not yet experience or display symptoms of the disease state; (ii) inhibiting the disease state, i.e., arresting the development of the disease state or its clinical symptoms; or (iii) relieving the disease state, i.e., causing temporary or permanent regression of the disease state or its clinical symptoms.

All patents and publications identified herein are incorporated herein by reference in their entirety.

COMPOUNDS AND PREPARATIONS

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

General Methods

The invention provides compounds and compositions for treating inflammatory disorders, and methods of treating disorders mediated by JNK.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reaction described herein preferably are conducted under inert atmosphere, at atmospheric pressure, at a reaction temperature range of from about −78° C. to about 180° C., and most preferably and conveniently at room (or ambient) temperature, e.g., about 20° C.

TABLE X

| Cmpd. No. | Structure | Nomenclature |
|---|---|---|
| 1 | 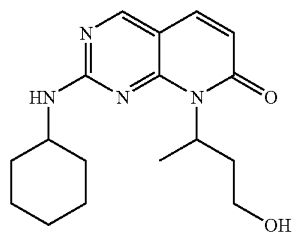 [SMILES: CC(CCO)n1c(=O)ccc2cnc(NC3CCCCC3)nc21] | 2-Cyclohexylamino-8-(3-hydroxy-1-methyl-propyl)-8H-pyrido[2,3-d]pyrimidin-7-one |
| 2 | 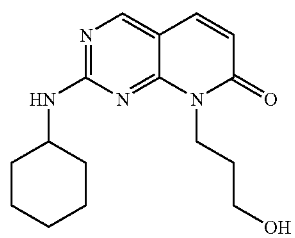 [SMILES: O=c1ccc2cnc(NC3CCCCC3)nc2n1CCCO] | 2-Cyclohexylamino-8-(3-hydroxy-propyl)-8H-pyrido[2,3-d]pyrimidin-7-one |
| 3 | 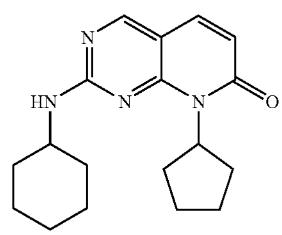 [SMILES: O=c1ccc2cnc(NC3CCCCC3)nc2n1C1CCCC1] | 2-Cyclohexylamino-8-cyclopentyl-8H-pyrido[2,3-d]pyrimidin-7-one |
| 4 | 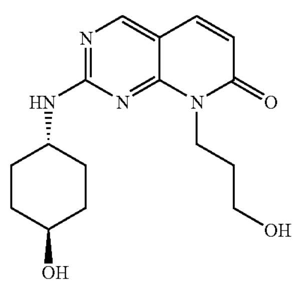 [SMILES: O=c1ccc2cnc(N[C@H]3CC[C@H](O)CC3)nc2n1CCCO] | 2-(4-Hydroxy-cyclohexylamino)-8-(3-hydroxy-propyl)-8H-pyrido[2,3-d]pyrimidin-7-one |

TABLE X-continued

| Cmpd. No. | Structure | Nomenclature |
|---|---|---|
| 5 | 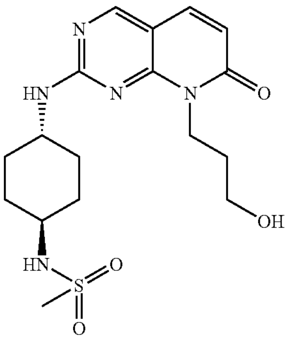 [SMILES: CS(=O)(=O)N[C@H]1CC[C@H](Nc2ncc3ccc(=O)n(CCCO)c3n2)CC1] | N-{4-[8-(3-Hydroxy-propyl)-7-oxo-7,8-dihydro-pyrido[2,3-d]pyrimidin-2-ylamino]-cyclohexyl}-methanesulfonamide |
| 6 | 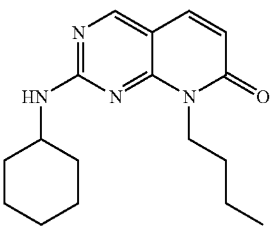 [SMILES: CCCCn1c(=O)ccc2cnc(NC3CCCCC3)nc21] | 8-Butyl-2-cyclohexylamino-8H-pyrido[2,3-d]pyrimidin-7-one |
| 7 | 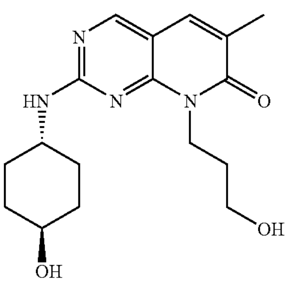 [SMILES: Cc1cc2cnc(N[C@H]3CC[C@H](O)CC3)nc2n(CCCO)c1=O] | 2-(4-Hydroxy-cyclohexylamino)-8-(3-hydroxy-propyl)-6-methyl-8H-pyrido[2,3-d]pyrimidin-7-one |
| 8 | 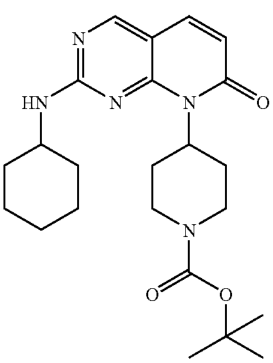 [SMILES: CC(C)(C)OC(=O)N1CCC(n2c(=O)ccc3cnc(NC4CCCCC4)nc32)CC1] | 4-(2-Cyclohexylamino-7-oxo-7H-pyrido[2,3-d]pyrimidin-8-yl)-piperidine-1-carboxylic acid tert-butyl ester |
| 9 | 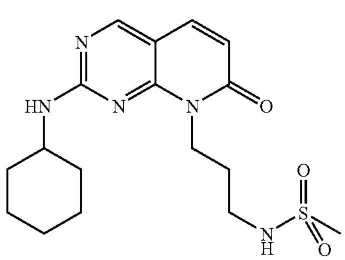 [SMILES: CS(=O)(=O)NCCCn1c(=O)ccc2cnc(NC3CCCCC3)nc21] | N-[3-(2-Cyclohexylamino-7-oxo-7H-pyrido[2,3-d]pyrimidin-8-yl)-propyl]-methanesulfonamide |

TABLE X-continued

| Cmpd. No. | Structure | Nomenclature |
| --- | --- | --- |
| 10 | 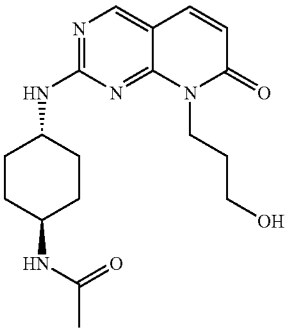 [SMILES: CC(=O)N[C@H]1CC[C@H](Nc2ncc3ccc(=O)n(CCCO)c3n2)CC1] | N-{4-[8-(3-Hydroxy-propyl)-7-oxo-7,8-dihydro-pyrido[2,3-d]pyrimidin-2-ylamino]-cyclohexyl}-acetamide |
| 11 | 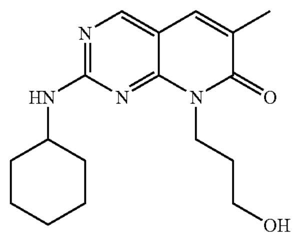 [SMILES: Cc1cc2cnc(NC3CCCCC3)nc2n(CCCO)c1=O] | 2-Cyclohexylamino-8-(3-hydroxy-propyl)-6-methyl-8H-pyrido[2,3-pyrimidin-7-one |
| 12 | 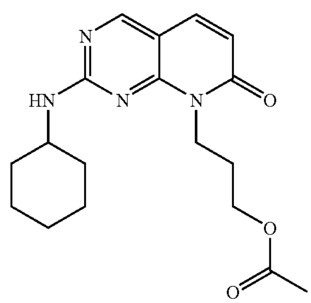 [SMILES: CC(=O)OCCCn1c(=O)ccc2cnc(NC3CCCCC3)nc21] | Acetic acid 3-(2-cyclohexylamino-7-oxo-7H-pyrido[2,3-d]pyrimidin-8-yl)-propyl ester |
| 13 | 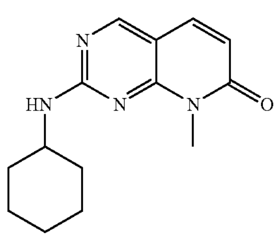 [SMILES: Cn1c(=O)ccc2cnc(NC3CCCCC3)nc21] | 2-Cyclohexylamino-8-methyl-8H-pyrido[2,3-d]pyrimidin-7-one |
| 14 | 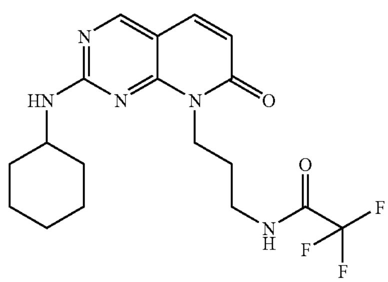 [SMILES: O=C(NCCCn1c(=O)ccc2cnc(NC3CCCCC3)nc21)C(F)(F)F] | N-[3-(2-Cyclohexylamino-7-oxo-7H-pyrido[2,3-d]pyrimidin-8-yl)-propyl]-2,2,2-trifluoro-acetamide |

TABLE X-continued

| Cmpd. No. | Structure | Nomenclature |
|---|---|---|
| 15 | 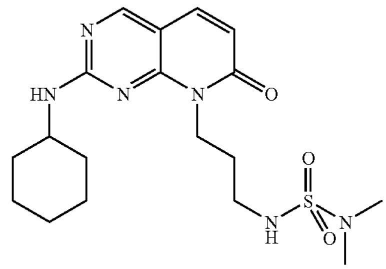 [SMILES: CN(C)S(=O)(=O)NCCCn1c(=O)ccc2cnc(NC3CCCCC3)nc21] | N-[3-(2-Cyclohexylamino-7-oxo-7H-pyrido[2,3-d]pyrimidin-8-yl)-propyl]-N,N-dimethylamino sulfonamide |
| 16 | 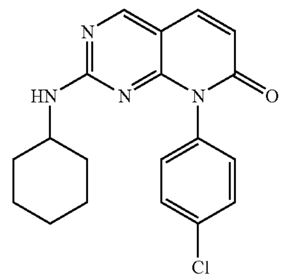 [SMILES: O=c1ccc2cnc(NC3CCCCC3)nc2n1-c1ccc(Cl)cc1] | 8-(4-Chloro-phenyl)-2-cyclohexylamino-8H-pyrido[2,3-d]pyrimidin-7-one |
| 17 | 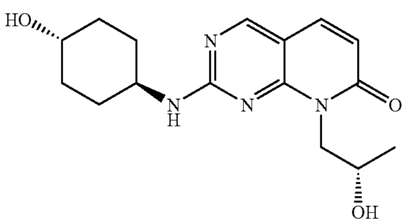 [SMILES: C[C@H](O)Cn1c(=O)ccc2cnc(N[C@H]3CC[C@H](O)CC3)nc21] | 2-(4-Hydroxy-cyclohexylamino)-8-((S)-2-hydroxy-propyl)-8H-pyrido[2,3-d]pyrimidin-7-one |
| 18 | 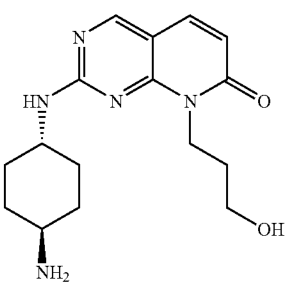 [SMILES: N[C@H]1CC[C@H](Nc2ncc3ccc(=O)n(CCCO)c3n2)CC1] | 2-(4-Amino-cyclohexylamino)-8-(3-hydroxy-propyl)-8H-pyrido[2,3-d]pyrimidin-7-one |
| 19 | 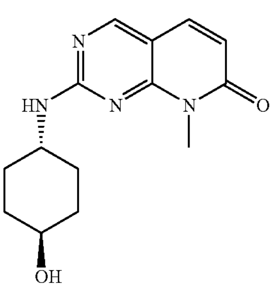 [SMILES: Cn1c(=O)ccc2cnc(N[C@H]3CC[C@H](O)CC3)nc21] | 2-(4-Hydroxy-cyclohexylamino)-8-methyl-8H-pyrido[2,3-d]pyrimidin-7-one |
| 20 | 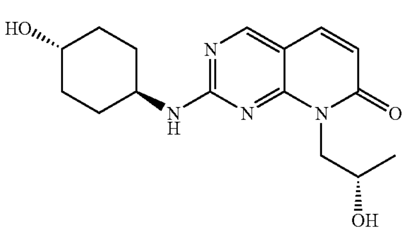 [SMILES: C[C@H](O)Cn1c(=O)ccc2cnc(N[C@H]3CC[C@H](O)CC3)nc21] | 2-(4-Hydroxy-cyclohexylamino)-8-((S)-2-hydroxy-propyl)-8H-pyrido[2,3-d]pyrimidin-7-one |

TABLE X-continued

| Cmpd. No. | Structure | Nomenclature |
|---|---|---|
| 21 | 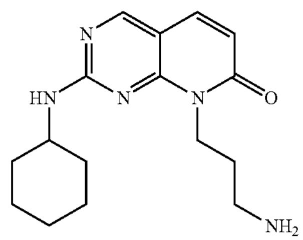 [SMILES: NCCCn1c(=O)ccc2cnc(NC3CCCCC3)nc21] | 8-(3-Amino-propyl)-2-cyclohexylamino-8H-pyrido [2,3-d]pyrimidin-7-one |
| 22 | 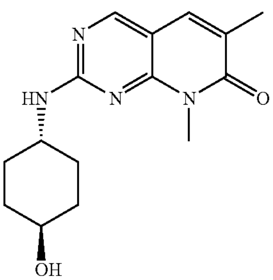 [SMILES: Cc1cc2cnc(N[C@H]3CC[C@H](O)CC3)nc2n(C)c1=O] | 2-(4-Hydroxy-cyclohexylamino)-6,8-dimethyl-8H-pyrido[2,3-d]pyrimidin-7-one |
| 23 | 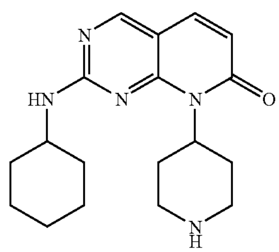 [SMILES: O=c1ccc2cnc(NC3CCCCC3)nc2n1C1CCNCC1] | 2-Cyclohexylamino-8-piperidin-4-yl-8H-pyrido[2,3-d]pyrimidin-7-one |
| 24 | 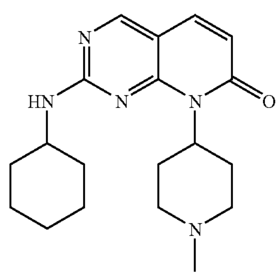 [SMILES: CN1CCC(n2c(=O)ccc3cnc(NC4CCCCC4)nc32)CC1] | 2-Cyclohexylamino-8-(1-methyl-piperidin-4-yl)-8H-pyrido[2,3-d]pyrimidin-7-one |
| 25 | 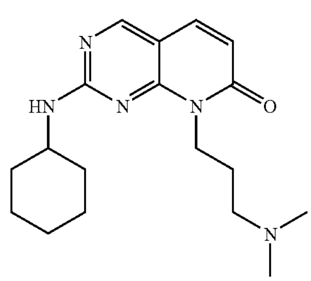 [SMILES: CN(C)CCCn1c(=O)ccc2cnc(NC3CCCCC3)nc21] | 2-Cyclohexylamino-8-(3-dimethylamino-propyl)-8H-pyrido[2,3-d]pyrimidin-7-one |

Utility

The compounds of this invention are JNK modulators and as such are expected to be effective in the treatment of a wide range of JNK mediated disorders. Exemplary JNK mediated disorders include, but are not limited to, autoimmune disorders, inflammatory disorders, metabolic disorders, neurological disease, and cancer. Accordingly, compounds of the invention can be used to treat one or more of such disorders. In some embodiments, compounds of the invention can be used to treat a JNK mediated disorder such as rheumatoid arthritis, asthma, type II diabetes, Alzheimer's disease, Parkinson's disease or stroke.

Administration and Pharmaceutical Compositions

The invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

Compounds of the invention may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use.

Formulations containing about one (1) mg of active ingredient or, more broadly, about 0.01 to about one hundred (100) mg, per tablet, are accordingly suitable representative unit dosage forms.

The compounds of the invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the invention may also be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention may be formulated for vaginal administration. Pessaries, tampons, creams, gels, pastes, foams or sprays containing in addition to the active ingredient such carriers as are known in the art to be appropriate.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacyclo-heptan-2-one). Sustained release delivery systems are inserted subcutaneously into the sub-dermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described below.

Additional objects, advantages, and novel features of this invention will become apparent to those skilled in the art upon examination of the following examples thereof, which are not intended to be limiting.

LIST OF ABBREVIATIONS

Ac$_2$O Acetic anhydride
AcOH Acetic acid
DBU 1,8-Diazabicyclo[5.4.0]undec-7-ene
DCE 1,2-Dichloroethane
DCM Dichloromethane/Methylene chloride
DIPEA Diisopropylethylamine
DMF N,N-dimethylformamide
DMSO Dimethyl sulfoxide
EDCI 1-(3-Dimethylaminopropyl)-3-ethylcarbodiimide hydrochloride
Et$_2$O Diethyl ether
EtOH Ethanol/Ethyl alcohol
EtOAc Ethyl acetate
HOBt 1-Hydroxybenzotriazole
LDA Lithium diisopropylamide
LiHMDS Lithium bis(trimethylsilyl)amide
m-CPBA 3-Chloroperoxybenzoic acid
MeOH Methanol/Methyl alcohol
MW Microwaves
NMP 1-Methyl-2-pyrrolidinone
PMB 4-Methoxy benzyl
RT Room temperature
TBME tent-Butyl methyl ether
TFA Trifluoroacetic acid
Tf$_2$O Trifluoromethanesulfonic anhydride
THF Tetrahydrofuran
TLC Thin layer chromatography

EXAMPLES

The following preparations and examples are given to enable those skilled in the art to more clearly understand and to practice the present invention. They should not be considered as limiting the scope of the invention, but merely as being illustrative and representative thereof.

Example 1

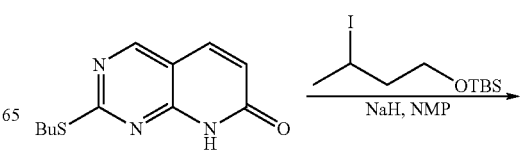

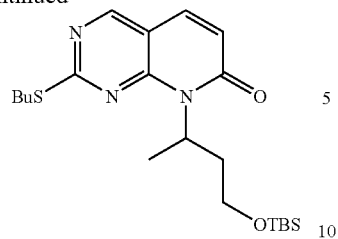

The pyridone (30 mg, 1.3 mmol) was dissolved in NMP, treated with NaH ((60%) 74 mg, 2.5 mmol) at r.t. and the iodide (1.2 g, 3.9 mmol) added and the mixture stirred for 3 hours. The reaction was then quenched with 3 mL H₂O, extracted with EtOAc (20 mL), washed with 10 mL 0.3% wt. aq. LiCl, dried with MgSO₄, filtered, and purified by flash chromatography (10:1 hexane:EtOAc) to give 5.3 mg of the product.

Example 2

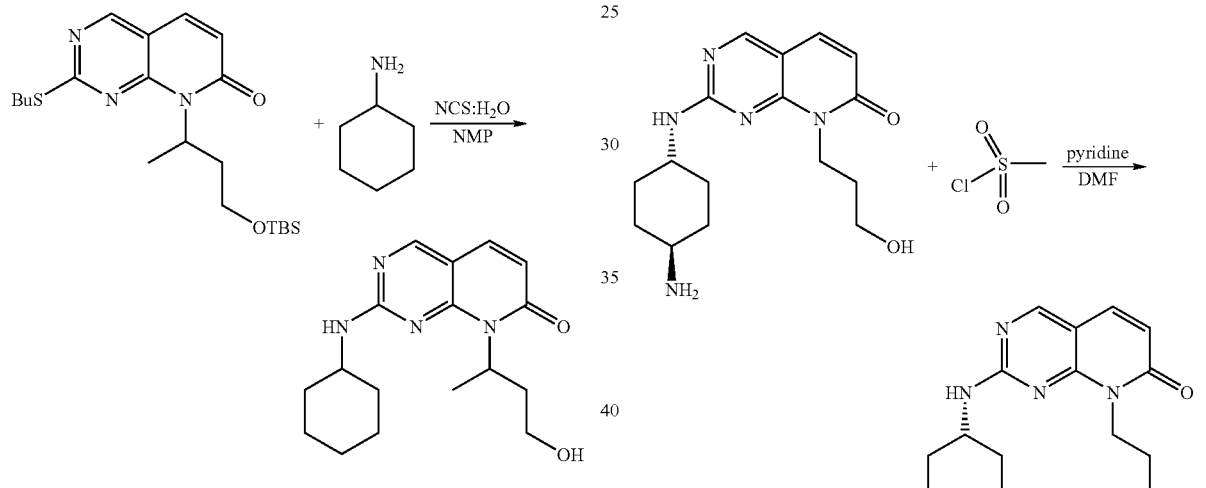

The thioether (300 mg, 0.71 mmol) was dissolved in NMP, treated with NCS (104 mg, 0.78 mmol) in NMP and 0.3 mL H₂O and heated at 80° C. for 15 min. The amine (0.16 mL, 1.4 mmol) was then added and the solution heated for another 40 min at 80° C. and then allowed to cool to r.t. The solution was extracted with EtOAc (40 mL), washed with 2×10 mL 0.3% wt. aq. LiCl, dried with MgSO₄, filtered, and purified by flash chromatography (4:1 hexane:EtOAc to 100% EtOAc) to give the product (M.P. 152.0-155.5 C, (M+H) 317).

Example 3

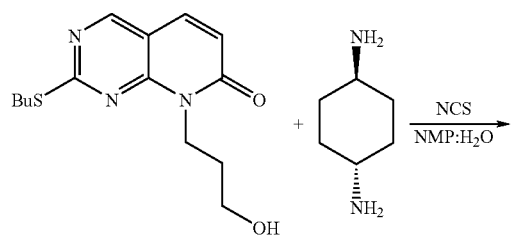

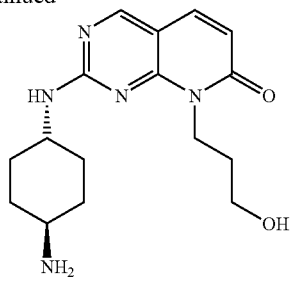

The pyridone (0.3 g, 1.0 mmol) was dissolved in NMP and NCS in NMP:H₂O added and heated at 70° C. and the diamine was added and heated at 70° C. for 1 h and allowed to cool. The resultant solid was filtered off and the solid washed with EtOAc to give crude product (0.24 g). The crude material was purified by prep. TLC using 60:10:1 CH₂Cl₂:MeOH:NH₄OH to give the product (0.08 g) ((M+H) 318).

Example 4

The pyridone (0.08 g, 0.25 mmol) was dissolved in DMF (5 mL) and pyridine (0.020 mL, 0.25) was subsequently added followed by MsCl (0.19 mL, 0.25 mmol) and the mixture was allowed to stir at r.t. for 2 h. The crude product was purified by prep. TLC using 60:10:1 CH₂Cl₂:MeOH:NH₄OH, then diluted in DCM, dried over MgSO₄, filtered and concentrated ((M+H) 396).

Example 5

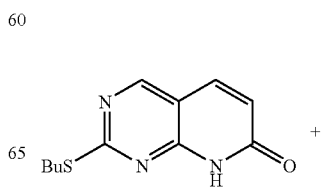

-continued

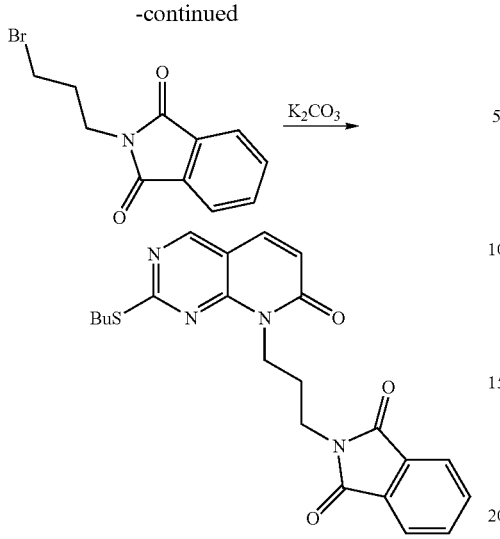

The pyridone (0.75 g, 3.2 mmol) was dissolved in DMF and K₂CO₃ (0.56 g, 4.1 mmol) was then added and allowed to stir overnight at r.t. The mixture was then worked up with EtOAc and 0.3% LiCl (aq.), dried over MgSO₄, filtered, concentrated and purified on a column using 1:2 EtOAc/hexane to give the product ((1.00 g, 74%) (M+H) 423).

Example 6

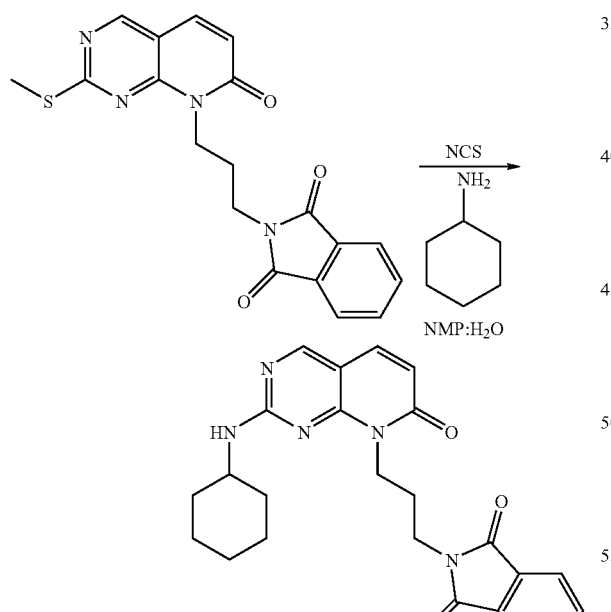

The pyridone (1.0 g, 2.4 mmol) in NMP (6 mL) was treated with NCS (0.33 g, 2.5 mmol) in NMP/H₂O and heated for 30 min at 70° C. and the amine (0.55 g, 2.5 mmol) was added and allowed to stir for 1 h. EtOAc/H₂O was then added to the mixture, the solid filtered off, washed with EtOAc and H₂O and dried in vacuo to yield the product (additional product obtained from workup of organic layer purified using prep. TLC 60:10:1 CH₂Cl₂:MeOH:NH₄OH) (0.63 g total yield) ((M+H) 432).

Example 7

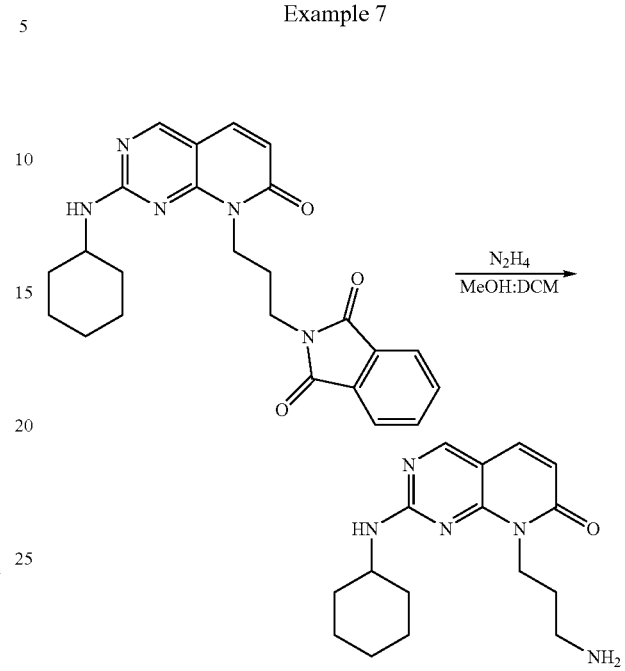

The pyridone (0.63 g, 1.5 mmol) was dissolved in 4 mL MeOH and 1 mL DCM, the hydrazine (0.056 mL, 1.75 mmol) was added and the mixture allowed to stir overnight at r.t. The resultant solid was filtered off, washed with DCM, and purified using prep TLC using 60:10:1 CH₂Cl₂:MeOH:NH₄OH to give the product (0.34 g, (M+H) 302).

Example 8

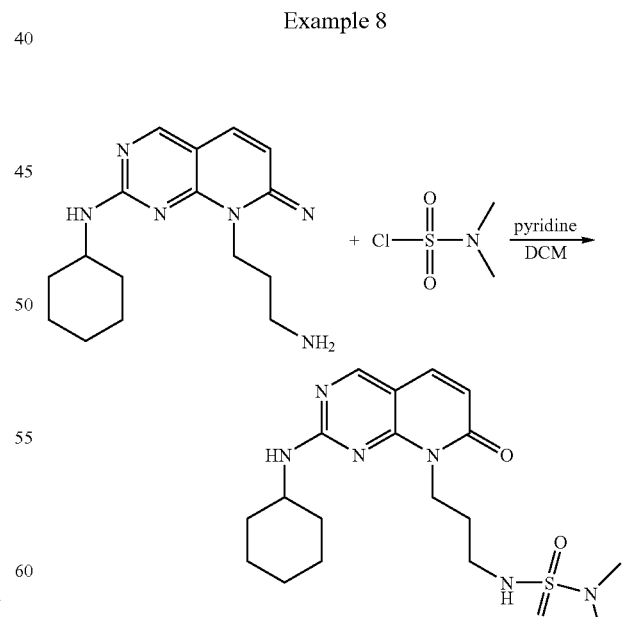

The pyridone (0.09 g, 0.3 mmol) was dissolved in DCM, the pyridine (0.024 mL, 0.3 mmol) added and dimethylsulfamoyl chloride (0.032 mL, 0.3 mmol) added and the mixture allowed to stir overnight at r.t. The product was purified using prep TLC using 60:10:1 CH₂Cl₂:MeOH:NH₄OH to give the product ((M+H) 409).

Example 9

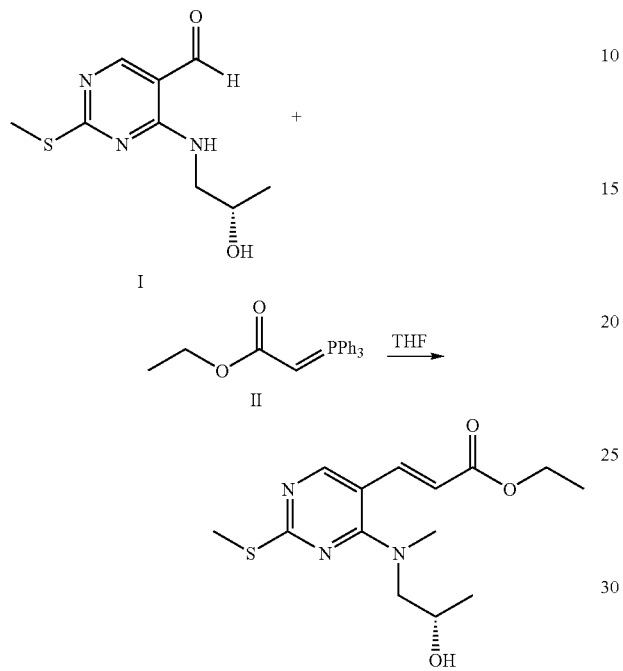

I (1.50 g) and II (2.99 g) were combined in THF under N₂, heated to reflux and allowed to stir for 19 h. The mixture was then concentrated and the product purified by chromatography using 40-50% EtOAc-hexane to give 1.62 g III (83%).

Example 10

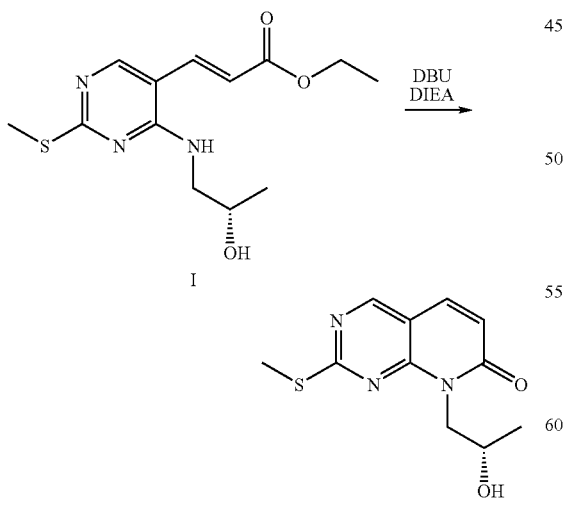

I (1.52 g), DBU (9 mL), DIEA (0.98 mL) were combined under N₂, heated to 120° C. and allowed to reflux for 1 h, heated at 100° C. for 1 h and then allowed to cool to r.t. The mixture was then poured into 50 mL EtOAc, 60 mL 1M HCL was then added and the organic layer then washed with 2×25 mL H₂O, dried over sodium sulfate, and concentrated to yield II (0.9 g).

Example 11

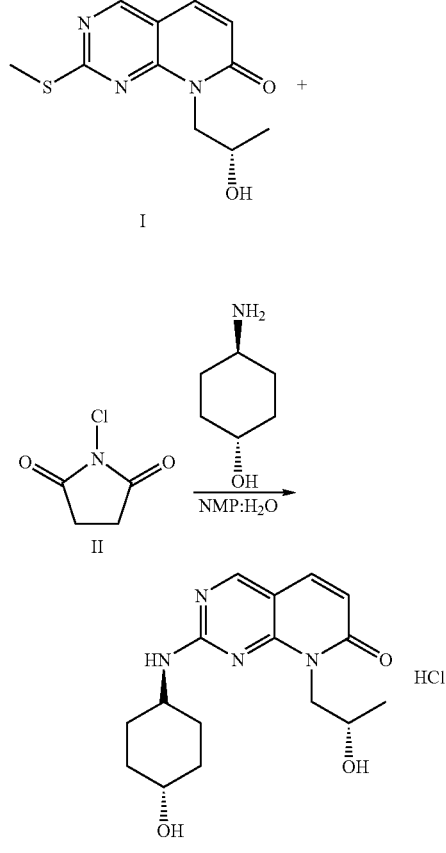

I (0.30 g) in 1 mL NMP was allowed to dissolve and II (0.17 g) in NMP (0.8 mL)/H₂O (0.8 mL) was then added and the reaction heated to 70° C. under N₂ for 15 min, the amine (0.27 g) was then added and the reaction heated to 100° C. for 30 min and subsequently cooled to r.t. 25 mL hexane was then added and the mixture stirred for 2 h and the hexane removed. The residue was then purified by chromatography using 0-20% MeOH/DCM to yield 0.25 g III.

Example 12

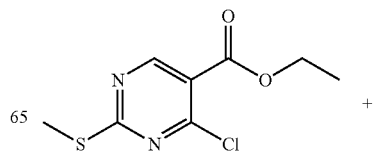

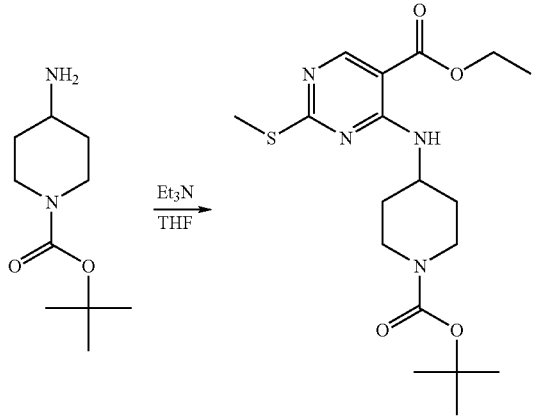

The pyrimidine (5.7 g, 24.4 mmol) was dissolved in THF, and the amine (5.9 g, 29.4 mmol) was then added and then treated with Et₃N, allowed to stir for 2.5 h, the solids filtered off, and the filtrate concentrated to yield the product with residual THF (11.22 g).

Example 13

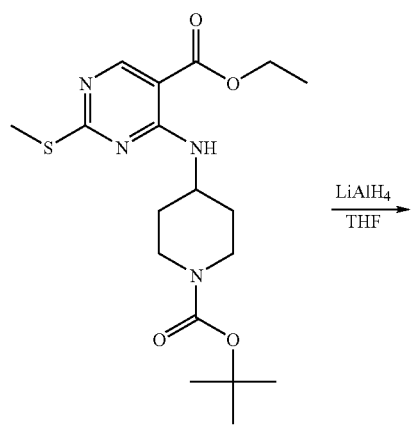

The pyrimidine (9.8 g, 24.4 mmol) was dissolved in 180 mL THF, cooled to −70° C. and LAH (26.8 mL 1.0M in THF) added and the reaction allowed to stir for 25 min and then cooled to −70° C. for 30 min and slowly allowed to reach 0° C. over several hours and quenched with 11.2 mL iPrOH and then 3.3 mL H₂O and filtered through celite, concentrated and purified on a column using 1:2 EtOAc/hexane-100% EtOAc to yield the product (5.0 g, 58%).

Example 14

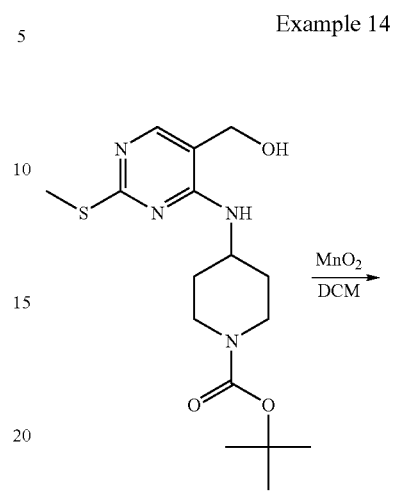

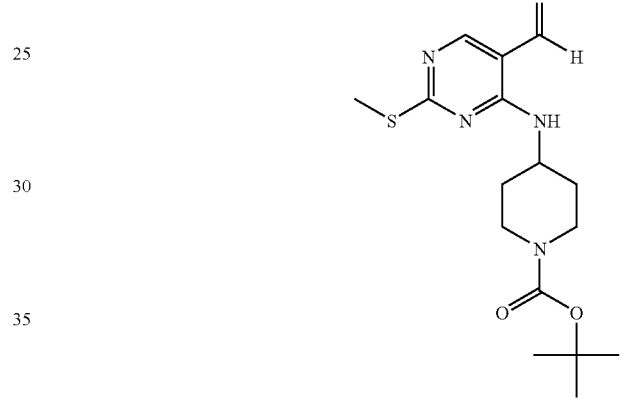

The alcohol (5.04 g, 14.2 mmol) was dissolved in 223 mL DCM and treated with MnO₂ (12.4 g, 142 mmol) under N₂ and stirred at r.t. for 3 h. The mixture was filtered through celite and flushed with DCM and the solution concentrated in vacuo to yield the product (4.73 g, 95%) ((M+H) 353).

Example 15

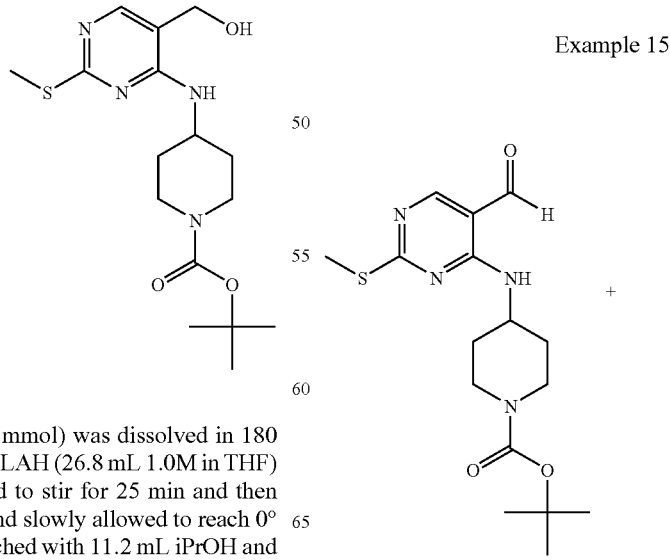

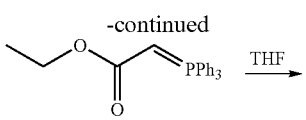 THF →

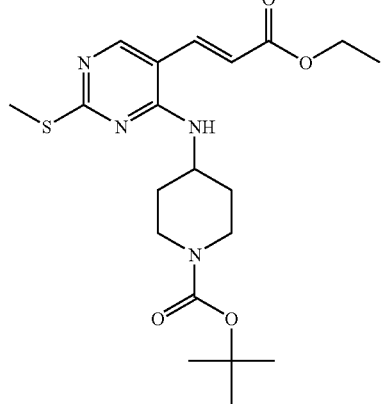

The aldehyde (4.73 g, 13.4 mmol) in 35 mL THF was treated with the phosphine (6.1 g, 17.4 mmol) and allowed to reflux at 80° C. and then cooled to r.t. and purified by chromatography on a column using 1:4 EtOAc/hexane to yield the product (5.31 g, 94%).

Example 16

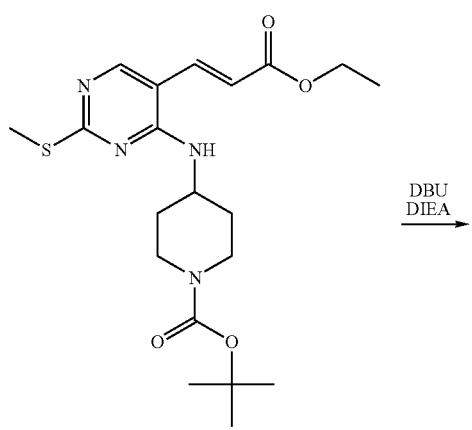
DBU
DIEA
→ organic layer isolated, dried over magnesium sulfate, and concentrated to crude product. The crude material was purified by chromatography using 60:10:1 $CH_2Cl_2$:MeOH:$NH_4OH$ to give the product (0.22 g, 17%) (M+H) 377).

Example 17

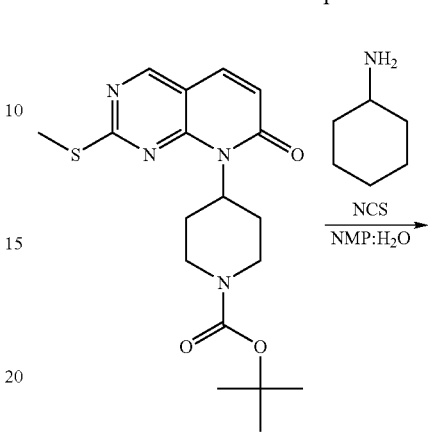

The pyridone (0.22 g, 0.58 mmol) was dissolved in 1 mL NMP, treated with NCS (0.081 g) in 0.6 mL NMP and 0.4 mL $H_2O$ and heated at 80° C. for 15 min. The amine (0.133 mL, 1.16 mmol) was then added and the solution heated for another 30 min at 80° C. and then allowed to cool to r.t. The resultant solid was filtered off, rinsed with EtOAc solution was extracted with EtOAc (40 mL), washed with 2×10 mL 0.3% wt. aq. LiCl, dried with $MgSO_4$, filtered, and purified by prep TLC using 60:10:1 $CH_2Cl_2$:MeOH:$NH_4OH$ to give the product (50 mg, M.P. 221.1-223.1 C, (M+H) 428).

Example 18

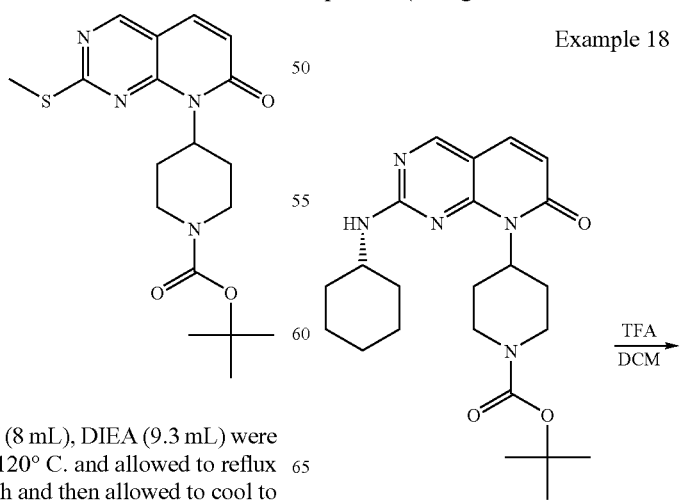

The pyrimidine (1.5 g), DBU (8 mL), DIEA (9.3 mL) were combined under $N_2$, heated to 120° C. and allowed to reflux for 1 h, heated at 100° C. for 1 h and then allowed to cool to r.t. The mixture was then extracted into EtOAc/$H_2O$, the -continued

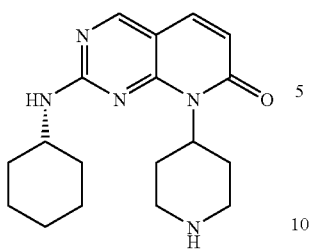

The pyridone (100 mg) was dissolved in 5 mL DCM and TFA (0.5 mL) added and allowed to stir for 2.5 h at r.t. and purified via prep. TLC using 60:10:1 CH$_2$Cl$_2$:MeOH:NH$_4$OH and the product obtained (M.P. 109.0-112.0° C.).

Example 19

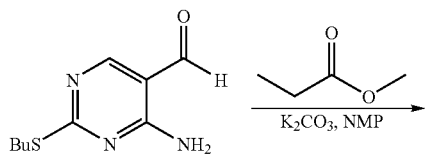

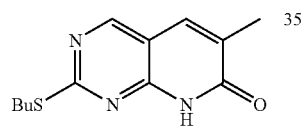

Methyl propionate was added to the aldehyde (2.0 g, 9.5 mmol) and K$_2$CO$_3$ (9.5 mmol) in NMP and heated to 120° C. and allowed to stir overnight. Methyl propionate (4.6 mL, 47.5 mmol)) and K$_2$CO$_3$ (9.5 mmol) were then added to the mixture and heated to 130° C. for 4 days. The reaction was then cooled to r.t., poured into EtOAc and H$_2$O added. The organic layer was then washed with 3×0.3% LiCl (aq.) and dried over MgSO$_4$, filtered, and concentrated to give the product (2.0 g, 75%).

Example 20

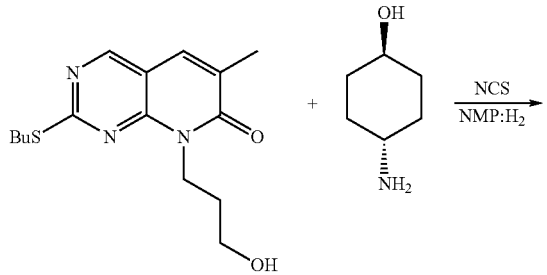

-continued

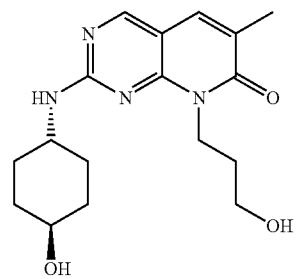

The pyridone (150 mg, 0.49 mmol) was dissolved in 0.4 mL NMP and treated with NCS (68 mg, 0.52 mmol) dissolved in 0.4 mL NMP and 0.2 mL H$_2$O and allowed to heat to 70° C. for 1 h. The mixture was allowed to cool to r.t. and added to EtOAc/H$_2$O/MeOH, and concentrated at 100° C. and purified the crude material with prep TLC using 60:10:1 CH$_2$Cl$_2$:MeOH:NH$_4$OH to yield the product ((M+H) 333).

Example 21

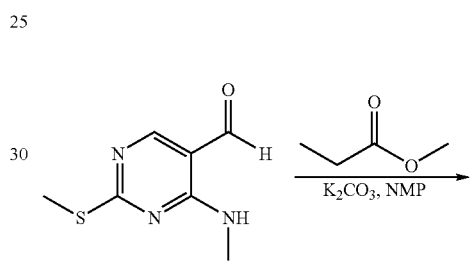

The aldehyde (1.6 g, 8.7 mmol) was dissolved in NMP and treated with the ester (4.2 mL, 43.7 mmol) and K$_2$CO$_3$ and heated in a sealed tube at 110° C. for 2 days. The mixture was then cooled to r.t., poured into EtOAc/H$_2$O, washed with 3×30 mL 0.3% LiCl (aq.), filtered, concentrated, and purified by flash chromatography using 4:1 to 1:1 hexane:EtOAc to yield the product (560 mg).

Example 22

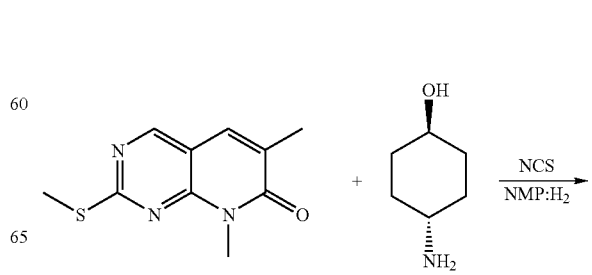

-continued
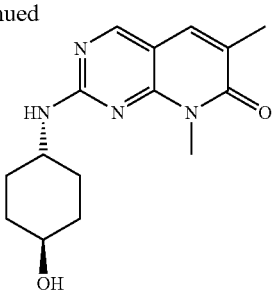
The thioether (300 mg, 1.3 mmol) was dissolved in NMP and treated with NCS (190 mg, 1.4 mL) in NMP:H$_2$O and heated to 80° C. for 20 min and the amine (312 mg, 2.7 mmol) added and allowed to stir for 2 h and then cooled to r.t. The mixture was then poured into 40 mL EtOAc and rinsed with 4×10 mL 0.3% LiCl (aq.), dried over MgSO$_4$, filtered, concentrated, and triturated with DCM to yield the product ((M+H) 289, M.P. 218.7-220.0° C.).
Example 23
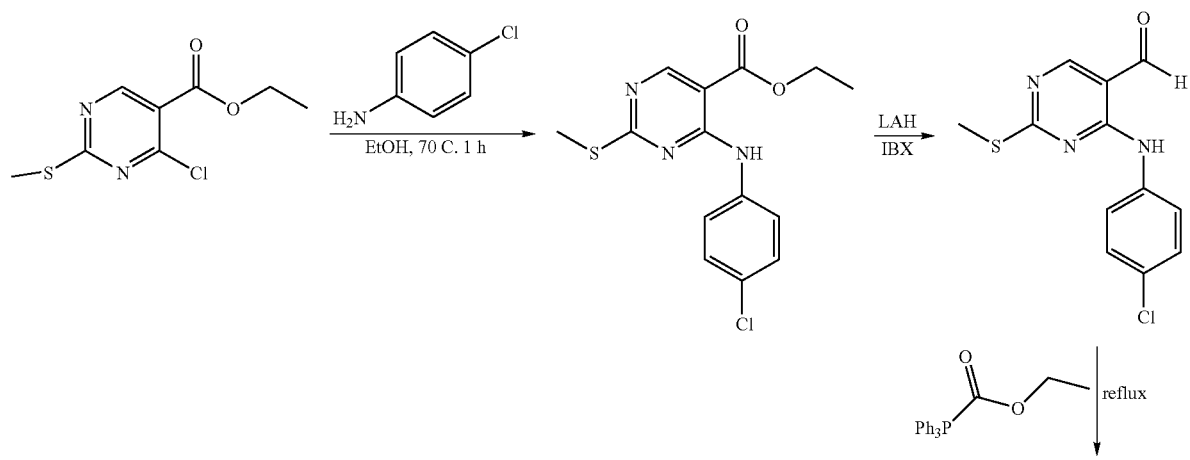
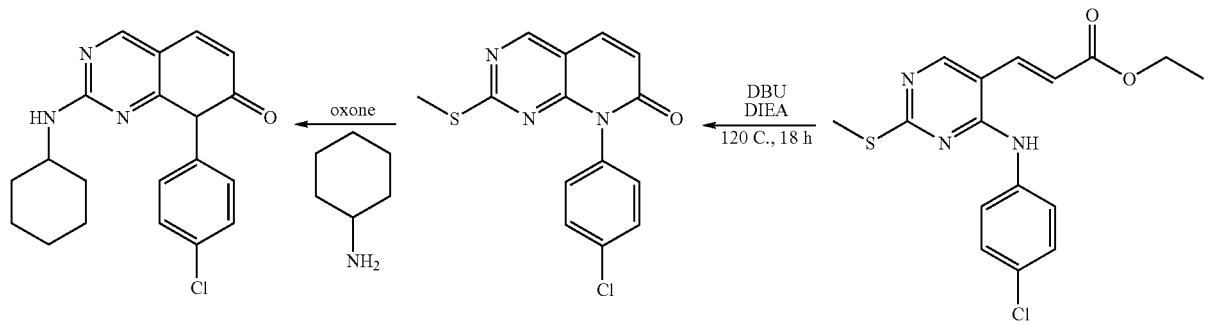

The reduction was carried out on a 2 g scale using LiAlH$_4$ and the desired alcohol was obtained in 98% yield. Oxidation to obtain the aldehyde in 68% yield was performed using freshly prepared IBX. The homologation reaction using carbethoxymethylene-triphenylphosphorane was carried out on a 2 g scale and the reaction complete after reflux for 1 h to obtain the a,b-unsaturated ester in 46% yield. The cyclization reaction was performed with DBU and Hunig's base as a solvent at 120° C. in 18 h, with acid work up and purification by chromatography to yield the cyclized derivative in 30% yield.

Biological Assays

Example 24

JNK Assay In Vitro

JNK activity was measured by phosphorylation of GST-ATF2 (19-96) with [γ-$^{33}$P] ATP. The enzyme reaction was conducted at Km concentrations of ATP and the substrate at final volume of 40 μl in buffer containing 25 mM HEPES, pH 7.5, 2 mM dithiothreitol, 150 mM NaCl, 20 mM MgCl$_2$, 0.001% Tween® 20, 0.1% BSA and 10% DMSO. Human JNK2α2 assay contains 1 nM enzyme, 1 μM ATF2, 8 μM ATP with 1 uCi [γ-$^{33}$P] ATP. Human JNK1α1 assay contains 2 nM enzyme, 1 μM ATF2, 6 μM ATP with 1 μCi [γ-$^{33}$P] ATP. Human JNK3 (Upstate Biotech #14-501M) assay contains 2 nM enzyme, 1 μM ATF2, 4 μM ATP with 1 μCi [γ-$^{33}$P] ATP. The enzyme assay was carried out in the presence or absence of several compound concentrations. JNK and compound were pre-incubated for 10 min., followed by initiation of the enzymatic reaction by adding ATP and the substrate. The reaction mixture was incubated at 30° C. for 30 min. At the end of incubation, the reaction was terminated by transferring 25 μl of the reaction mixture to 150 μl of 10% glutathione Sepharose® slurry (Amersham # 27-4574-01) containing 135 mM EDTA. The reaction product was captured on the affinity resin, and washed on a filtration plate (Millipore, MABVNOB50) with phosphate buffered saline for six times to remove free radionucleotide. The incorporation of $^{33}$P into ATF2 was quantified on a microplate scintillation counter (Packard Topcount). Compound inhibition potency on JNK was measured by IC$_{50}$ value generated from ten concentration inhibition curves fitted into the 3-parameter model: % inhibition=Maximum/(1+(IC$_{50}$/[Inhibitor])$^{slope}$). Data were analyzed on Microsoft Excel for parameter estimation. Representative results are shown in Table Y below:

TABLE Y

Representative Compound IC$_{50}$'s for JNK1 and JNK2

| Compound | JNK1 (μM) | JNK2 (μM) |
|---|---|---|
| 1 | 0.0701 | 0.1536 |
| 3 | 0.1076 | 0.1365 |
| 5 | 0.2822 | 0.7784 |
| 7 | 0.2912 | 0.4092 |
| 9 | 0.4638 | 0.6246 |
| 11 | 0.5034 | 0.7134 |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound according to Formula I

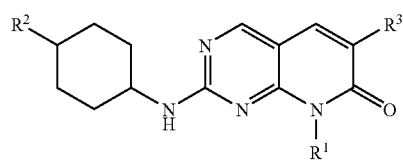

wherein:

R$^1$ is —Y—R$^{1'}$;

Y is lower alkylenyl, cycloalkylenyl, heterocycloalkylenyl, or phenylenyl;

R$^{1'}$ is hydroxy, OC(=O)R$^{1''}$, NHC(=O)R$^{1''}$, C(=O)OR$^{1''}$, NHSO$_2$R$^{1''}$, or N(R$^{1'''}$)$_2$, R$^{1''}$ is H, lower alkyl, amino, or lower haloalkyl;

each R$^{1'''}$ is independently H or lower alkyl;

R$^2$ is H or R$^{2'}$;

R$^{2'}$ is hydroxy, N(R$^{2''}$)$_2$, NHSO$_2$R$^{2''}$ or amido;

each R$^{2''}$ is independently H or lower alkyl; and

R$^3$ is H or methyl.

2. The compound of claim 1, wherein Y is lower alkylenyl.

3. The compound of claim 2, wherein R$^2$ is H.

4. The compound of claim 1, wherein Y is cycloalkylenyl.

5. The compound of claim 1, wherein Y is heterocycloalkylenyl.

6. The compound of claim 1, selected from the group consisting of:

2-Cyclohexylamino-8-(3-hydroxy-1-methyl-propyl)-8H-pyrido[2,3-d]pyrimidin-7-one;
2-Cyclohexylamino-8-(3-hydroxy-propyl)-8H-pyrido[2,3-d]pyrimidin-7-one;
2-(4-Hydroxy-cyclohexylamino)-8-(3-hydroxy-propyl)-8H-pyrido[2,3-d]pyrimidin-7-one;
N-{4-[8-(3-Hydroxy-propyl)-7-oxo-7,8-dihydro-pyrido[2,3-d]pyrimidin-2-ylamino]-cyclohexyl}-methanesulfonamide;
2-(4-Hydroxy-cyclohexylamino)-8-(3-hydroxy-propyl)-6-methyl-8H-pyrido[2,3-d]pyrimidin-7-one;
4-(2-Cyclohexylamino-7-oxo-7H-pyrido[2,3-d]pyrimidin-8-yl)-piperidine-1-carboxylic acid tert-butyl ester;
N-[3-(2-Cyclohexylamino-7-oxo-7H-pyrido[2,3-d]pyrimidin-8-yl)-propyl]-methanesulfonamide;
N-{4-[8-(3-Hydroxy-propyl)-7-oxo-7,8-dihydro-pyrido[2,3-d]pyrimidin-2-ylamino]-cyclohexyl}-acetamide;
2-Cyclohexylamino-8-(3-hydroxy-propyl)-6-methyl-8H-pyrido[2,3-d]pyrimidin-7-one;
Acetic acid 3-(2-cyclohexylamino-7-oxo-7H-pyrido[2,3-d]pyrimidin-8-yl)-propyl ester;
N-[3-(2-Cyclohexylamino-7-oxo-7H-pyrido[2,3-d]pyrimidin-8-yl)-propyl]-2,2,2-trifluoro-acetamide;
N-[3-(2-Cyclohexylamino-7-oxo-7H-pyrido[2,3-d]pyrimidin-8-yl)-propyl]-N,N-dimethylaminosulfonamide;
8-(4-Chloro-phenyl)-2-cyclohexylamino-8H-pyrido[2,3-d]pyrimidin-7-one
2-(4-Hydroxy-cyclohexylamino)-8-((S)-2-hydroxy-propyl)-8H-pyrido[2,3-d]pyrimidin-7-one;
2-(4-Amino-cyclohexylamino)-8-(3-hydroxy-propyl)-8H-pyrido[2,3-d]pyrimidin-7-one;
2-(4-Hydroxy-cyclohexylamino)-8-methyl-8H-pyrido[2,3-d]pyrimidin-7-one;

-continued 2-(4-Hydroxy-cyclohexylamino)-8-((S)-2-hydroxy-propyl)-8H-pyrido[2,3-d]pyrimidin-7-one;
8-(3-Amino-propyl)-2-cyclohexylamino-8H-pyrido[2,3-d]pyrimidin-7-one;
2-(4-Hydroxy-cyclohexylamino)-6,8-dimethyl-8H-pyrido[2,3-d]pyrimidin-7-one;
2-Cyclohexylamino-8-piperidin-4-yl-8H-pyrido[2,3-d]pyrimidin-7-one;
2-Cyclohexylamino-8-(1-methyl-piperidin-4-yl)-8H-pyrido[2,3-d]pyrimidin-7-one; and
2-Cyclohexylamino-8-(3-dimethylamino-propyl)-8H-pyrido[2,3-d]pyrimidin-7-one.

7. A compound according to Formula I

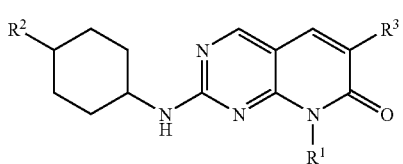

wherein:

$R^1$ is —Y—$R^{1'}$;
  Y is lower alkylenyl, cycloalkylenyl, heterocycloalkylenyl, or phenylenyl;

$R^{1'}$ is H, hydroxy, OC(=O)$R^{1''}$, NHC(=O)$R^{1''}$, C(=O)O$R^{1''}$, NHSO$_2$$R^{1''}$, or N($R^{1'''}$)$_2$, $R^{1''}$ is H, lower alkyl, amino, or lower haloalkyl;
  each $R^{1'''}$ is independently H or lower alkyl;

$R^2$ is hydroxy, N($R^{2''}$)$_2$, NHSO$_2$$R^{2''}$ or amido;
  each $R^{2''}$ is independently H or lower alkyl; and
$R^3$ is H or methyl;
or a pharmaceutically acceptable salt thereof.

* * * * *